(12) United States Patent
Maeda et al.

(10) Patent No.: US 10,973,593 B2
(45) Date of Patent: Apr. 13, 2021

(54) CENTRALIZED CONTROL APPARATUS

(71) Applicant: OLYMPUS CORPORATION, Hachioji (JP)

(72) Inventors: Yorito Maeda, Kiyose (JP); Kiyoshi Sekiguchi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 332 days.

(21) Appl. No.: 15/984,749

(22) Filed: May 21, 2018

(65) Prior Publication Data

US 2018/0263715 A1    Sep. 20, 2018

Related U.S. Application Data

(63) Continuation of application No. PCT/JP2016/080503, filed on Oct. 14, 2016.

(30) Foreign Application Priority Data

Nov. 30, 2015    (JP) .............................. JP2015-233718

(51) Int. Cl.
*A61B 1/00*    (2006.01)
*A61B 1/045*    (2006.01)
(Continued)

(52) U.S. Cl.
CPC ............ *A61B 34/25* (2016.02); *A61B 1/0005* (2013.01); *A61B 1/00006* (2013.01);
(Continued)

(58) Field of Classification Search
CPC ..... A61B 34/25; A61B 34/00; A61B 1/00006; A61B 1/00039; A61B 1/0005; A61B 1/04;
(Continued)

(56) References Cited

U.S. PATENT DOCUMENTS 8,443,279 B1 * 5/2013 Hameed .............. G06F 16/7867
715/230
9,980,629 B2 * 5/2018 King ..................... G06F 19/321
(Continued)

FOREIGN PATENT DOCUMENTS

| JP | 2003-175043 A | 6/2003 |
| JP | 2006-81664 A | 3/2006 |
| WO | 2015/087612 A1 | 6/2015 |

OTHER PUBLICATIONS

May 29, 2018 Office Action issued in Japanese Patent Application No. 2017-553689.
(Continued)

*Primary Examiner* — Timothy J Neal
*Assistant Examiner* — William B Chou
(74) *Attorney, Agent, or Firm* — Oliff PLC

(57) ABSTRACT

A centralized control apparatus is a centralized control apparatus configured to operate in a centralized manner, one or more operated devices used in a medical action, and includes a specification section configured to specify at least one of an operator and a procedure, an end operation section configured to receive an end operation to end the centralized operation of the operated device when the medical action ends, a recording section configured to record information on an operated device for which an end operation is necessary in association with at least one of the operator and the procedure, and a control section configured to, when the end operation section receives the end operation, acquire and execute setting items of an end process on the operated device linked by the recording section based on the specification result of the specification section.

7 Claims, 13 Drawing Sheets

(51) Int. Cl.
*A61B 1/04* (2006.01)
*A61B 34/00* (2016.01)
*G16H 40/67* (2018.01)
*G16H 40/20* (2018.01)
*G16H 15/00* (2018.01)
*A61B 1/06* (2006.01)
*A61B 17/00* (2006.01)
*G16H 40/60* (2018.01)

(52) U.S. Cl.
CPC ............ *A61B 1/00039* (2013.01); *A61B 1/04* (2013.01); *A61B 1/045* (2013.01); *A61B 1/0661* (2013.01); *A61B 17/00234* (2013.01); *A61B 34/00* (2016.02); *G16H 15/00* (2018.01); *G16H 40/20* (2018.01); *G16H 40/67* (2018.01); *A61B 1/00045* (2013.01); *A61B 2017/00017* (2013.01); *A61B 2034/254* (2016.02); *A61B 2560/0487* (2013.01); *G16H 40/60* (2018.01)

(58) Field of Classification Search
CPC . A61B 1/045; A61B 1/0661; A61B 17/00234; A61B 2034/254; A61B 2017/00017; A61B 2560/0487; G16H 40/67; G16H 40/20; G16H 40/60; G16H 15/00
See application file for complete search history.

(56) References Cited

U.S. PATENT DOCUMENTS

| | | | |
|---|---|---|---|
| 2004/0086163 A1* | 5/2004 | Moriyama | A61B 6/566 382/131 |
| 2004/0107113 A1* | 6/2004 | Araki | A61B 1/00006 600/118 |
| 2010/0042003 A1* | 2/2010 | Shiibashi | A61B 6/4494 600/476 |
| 2010/0238278 A1* | 9/2010 | Rovegno | A61B 1/042 348/75 |
| 2011/0178820 A1* | 7/2011 | Soni | G16H 50/20 705/3 |
| 2012/0200683 A1* | 8/2012 | Oshima | G06T 11/60 348/65 |
| 2013/0293694 A1* | 11/2013 | Mizobe | G16H 40/67 348/77 |
| 2013/0317376 A1* | 11/2013 | Saba | A61B 5/0464 600/509 |
| 2014/0160894 A1* | 6/2014 | Tobias | B06B 1/0207 367/137 |
| 2016/0275246 A1 | 9/2016 | Okusawa et al. | |

OTHER PUBLICATIONS

Dec. 20, 2016 International Search Report issued in International Application No. PCT/JP2016/080503.

* cited by examiner

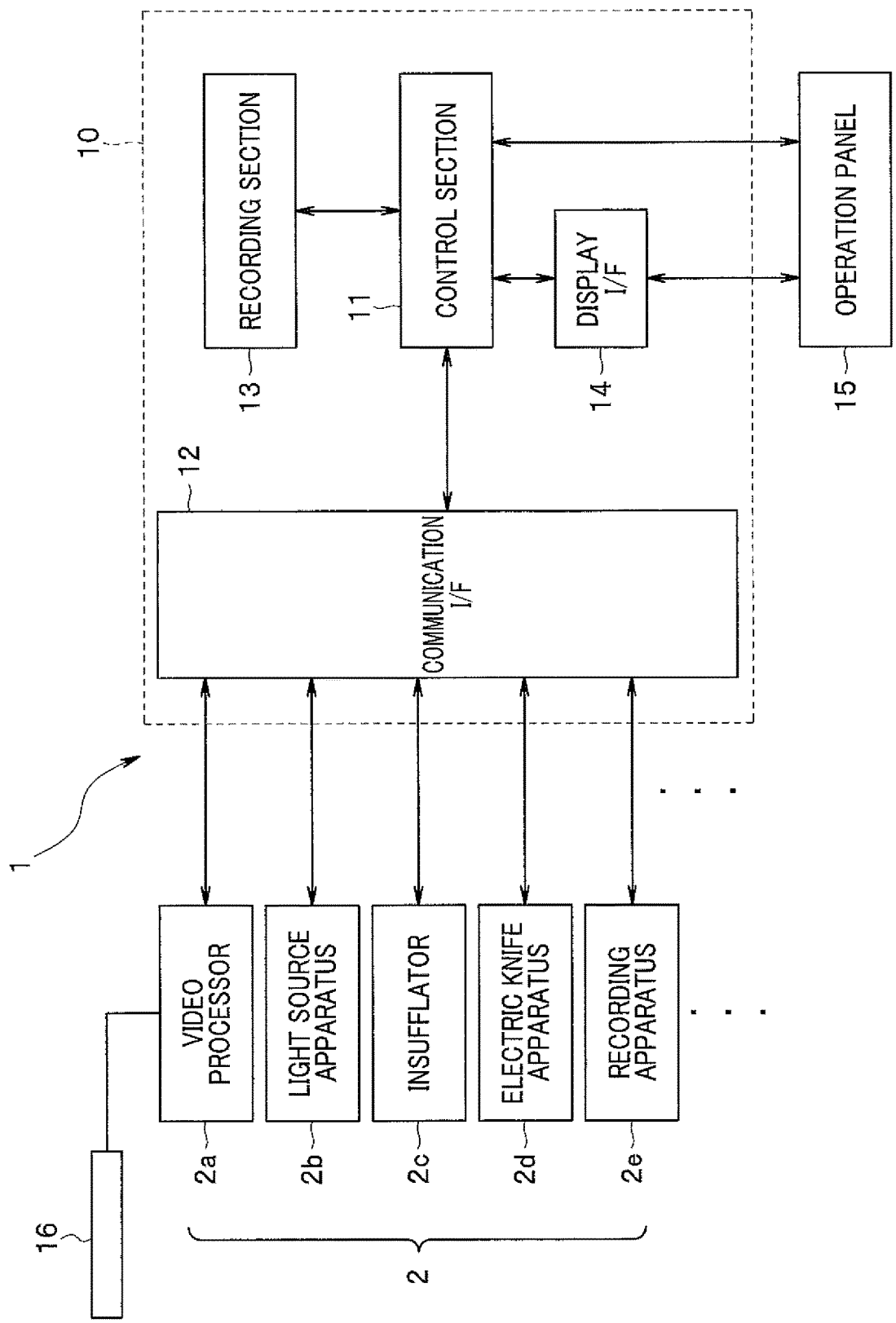

FIG. 2

| OPERATOR INFORMATION | Dr. Maeda | |
|---|---|---|
| PROCEDURE INFORMATION | LAPAROSCOPIC CHOLECYSTECTOMY | |

| SETTING ITEM LIST | | |
|---|---|---|
| DEVICE | FUNCTION | SET VALUE |
| RECORDING APPARATUS | RECORDING | STOP |
| RECORDING APPARATUS | CLOSE FOLDER | ON |
| VIDEO PROCESSOR | PROCEDURE END | ON |

| OPERATOR INFORMATION | Dr. Sekiguchi | |
|---|---|---|
| PROCEDURE INFORMATION | LADG | |

| SETTING ITEM LIST | | |
|---|---|---|
| DEVICE | FUNCTION | SET VALUE |
| RECORDING APPARATUS | RECORDING | STOP |
| RECORDING APPARATUS | CLOSE FOLDER | ON |
| VIDEO PROCESSOR | PROCEDURE END | ON |
| TV CONFERENCE SYSTEM | CUT | ON |
| ROOM CAMERA | POWER | OFF |

CENTRALIZED CONTROL APPARATUS

CROSS REFERENCE TO RELATED APPLICATION

This application is a continuation application of PCT/JP2016/080503 filed on Oct. 14, 2016 and claims benefit of Japanese Application No. 2015-233718 filed in Japan on Nov. 30, 2015, the entire contents of which are incorporated herein by this reference.

BACKGROUND OF THE INVENTION

1. Field of the Invention

The present invention relates to a centralized control apparatus that can remotely control a medical instrument.

2. Description of the Related Art

Conventionally, medical systems are proposed which adopt a system controller for controlling a medical instrument such as an endoscope used in surgery. A variety of medical instruments exist in an operating room such as an endoscope, a video processor, an electric knife, an insufflator, a recording apparatus and a display. Although the devices can be operated individually, it is troublesome for an operator or a nurse to move to the respective positions of the devices to operate the devices during surgery. Therefore, a system controller is adopted, which collectively operates the devices in the operating room.

The system controller is provided with an operation panel to perform centralized operation on each medical instrument. An operation screen of the system controller can display an operation screen specific to each device or an operation screen for collectively operating a plurality of devices or the like and a user can operate each device and make a setting for each device in the operating room using the operation screens of the system controller.

While the system controller can collectively operate the respective devices, the system controller does not manage all information on the surgery (medical action) or control of the respective devices in a centralized manner. For example, patient information on a patient who is the surgery target is managed by a video processor that processes images from an endoscope in the operating room. The patient information or information on the surgery on that day or the like is accumulated in a server in a hospital and the video processor maintains the patient information by reading the information.

Operation of loading the patient information into the video processor can also be performed using the system controller. When operating the devices used for surgery, a nurse or the like needs only to operate the system controller. With the system controller, it is possible to switch and display a necessary operation screen for each operator or for each procedure, and by using the operation screens of the system controller, the nurse or the like can relatively easily operate the devices necessary for surgery and need not master operations of the individual devices.

Settings necessary for each device for each surgery are different, and the user needs to make necessary settings or the like by operating the system controller every time surgery is changed. For example, during an end operation of the system controller, operations such as stopping recording of a recording apparatus, initialization of patient information for a next surgery and new reading of the patient information are necessary.

SUMMARY OF THE INVENTION

A centralized control apparatus according to an aspect of the present invention is a centralized control apparatus configured to operate in a centralized manner, one or more operated devices used in a medical action, including a specification section configured to specify at least one of an operator and a procedure, an end operation section configured to receive an end operation to end a centralized operation of each of the operated devices when the medical action ends, a recording section configured to record information on an operated device for which an end operation is necessary in association with at least one of the operator and the procedure, and a control section configured to, when the end operation section receives the end operation, acquire and execute setting items of an end process on the operated device linked by the recording section based on the specification result of the specification section.

Furthermore, a centralized control apparatus according to another aspect of the present invention is a centralized control apparatus configured to operate in a centralized manner, one or more operated devices used in a medical action, including an operator specification section configured to specify an operator, a procedure specification section configured to specify a procedure, an end operation section configured to receive an end operation to end a centralized operation of each of the operated devices when the medical action ends, a recording section configured to record information on an operated device for which an end operation is necessary in association with a combination of the operator and the procedure and a control section configured to, when the end operation section receives the end operation, acquire and execute setting items of an end process on the operated device linked by the recording section based on the specification result of the operator specification section and the specification result of the procedure specification section.

BRIEF DESCRIPTION OF THE DRAWINGS

FIG. 1 is a block diagram illustrating a medical system using a centralized control apparatus of the present invention;

FIG. 2 is a table illustrating contents of an example of setting information stored in a recording section 13;

DETAILED DESCRIPTION OF THE PREFERRED EMBODIMENTS

Figure 3:
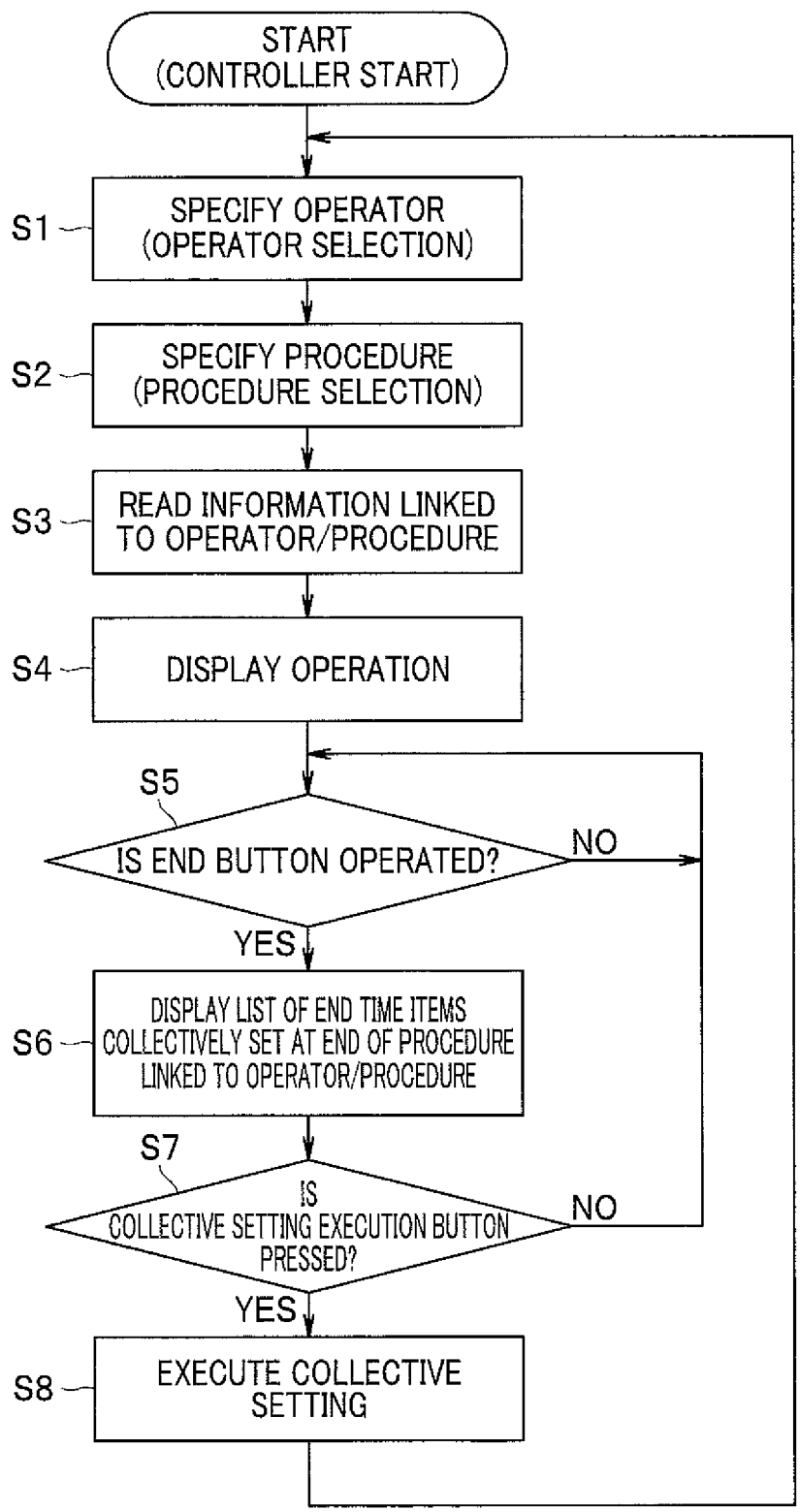
FIG. 3 is a flowchart for describing operation of the embodiment.

Hereinafter, embodiments of the present invention will be described with reference to the accompanying drawings.

First Embodiment

A system controller which is a centralized control apparatus is intended to perform centralized operation on various medical instruments arranged, for example, in an operating room, and logging on the system controller allows a user to perform centralized operation on the respective medical instruments and logging off the system controller allows the user to end the centralized operation on the respective medical instruments. To enable an optimum operation suited to each procedure or each operator, the system controller is configured to read setting information for centralized operation for each procedure. That is, the system controller registers an operator and a procedure at the time of logon. Thus, the system controller can display an operation screen suitable for the operator and the procedure on an operation panel.

In order to prevent control not intended by the operator on each medical instrument to be operated, the system controller is prevented from exercising control on each medical instrument other than control based on the user operation on the system controller, and the system controller and each medical instrument are designed to operate independently of each other. Therefore, when surgery or the like ends, power of each of the other medical instruments is not turned off even when a log-off operation of the system controller is performed or such a log-off operation will not cause the other medical instruments to receive some control. For the reason, when log-off is performed without initializing patient information or the like, the patient information at the time of log-on remains in the video processor. If the system controller is logged on again in the condition, the patient information of the previous surgery may be taken over and new surgery or the like may be conducted.

The present embodiment displays and executes a list of end process items to be executed at an end of a procedure at the time of log-off of the system controller and thereby supports implementation of reliable end process.

FIG. 1 is a block diagram illustrating a medical system using a centralized control apparatus of the present invention.

In FIG. 1, a medical system 1 of the present embodiment is provided with an operated device 2 composed of a plurality of medical instruments and a system controller 10. Although FIG. 1 illustrates a video processor 2a, a light source apparatus 2b, an insufflator 2c, an electric knife apparatus 2d and a recording apparatus 2e as the operated device 2, other various types of devices that can be arranged in an operating room or the like can also be adopted. The system controller 10 is provided with an operation panel 15 configured to receive operations by an operator such as a nurse.

The system controller 10 is enabled to perform centralized operation on the video processor 2a, the light source apparatus 2b, the insufflator 2c, the electric knife apparatus 2d and the recording apparatus 2e. When communication is in progress between the system controller 10 and the apparatuses, the system controller 10 is enabled to display setting conditions of the connected apparatuses and setting screens of operation switches or the like on a display screen of the operation panel 15. Furthermore, the system controller 10 is enabled to receive operations to change set values when a desired operation switch is touched and a touch panel in a predetermined region is operated.

The system controller 10 is provided with a communication I/F 12 for carrying out communication with each unit of the operated device 2. The communication I/F 12 can transmit signals through serial communication such as RS-232C or infrared rays. The communication I/F 12 can transmit a signal for driving each unit of operated device 2 from the control section 11 to the operated device 2.

The system controller 10 includes the control section 11 composed of a processor such as a CPU. The control section 11 controls operation of the entire system controller 10. Furthermore, the control section 11 is enabled to control a display I/F 14 and cause an operation display for receiving a GUI operation of the user to be displayed on a display screen of the operation panel 15. Note that display data for displaying the operation display is stored in the recording section 13, and the display I/F 14 receives the display data stored in the recording section 13 from the control section 11, generates display data for the operation display according to the control of the control section 11 and gives the display data to the operation panel 15.

The operation panel 15 is configured to display the operation display from the display I/F 14 on the display screen under the control of the control section 11. The operation panel 15 is provided with a touch panel which is not shown on the display screen, and when the operator touches each display part of the operation display via the touch panel, the operation panel 15 generates an operation signal corresponding to a GUI operation on each display part and outputs the operation signal to the control section 11. The control section 11 generates a control signal for controlling the operated device 2 based on the operation signal from the operation panel 15 and outputs the control signal to the corresponding operated device 2 via the communication I/F 12. Furthermore, the control section 11 can also acquire operation information indicating an operation condition of each unit of the operated device 2 via the communication I/F 12, change the operation display on the operation panel 15 to a display reflecting the operation information and display the operation information.

For example, the control section 11 is enabled to display a device selection display for selecting which peripheral device should be operated as the operated device 2 or a display for operating a selected unit of the operated device 2 as an operation display. Furthermore, the control section 11 is enabled to display an end display for indicating an end of a procedure as an operation display.

In the present embodiment, upon detecting that the end of the procedure is instructed by an operation by a nurse or the like on the end display, the control section 11 reads setting information for displaying an operation display (hereinafter referred to as "an end time setting item list display") for an end process from the recording section 13 and gives the display data to the display I/F 14. The display I/F 14 generates the end time setting item list display based on the display data and gives the end time setting item list display to the operation panel 15.

FIG. 2 is a table illustrating contents of an example of the setting information stored in the recording section 13. As shown in FIG. 2, the end process varies in contents from one operator or procedure to another. The example in FIG. 2 shows examples of the end process setting information on a procedure laparoscopic cholecystectomy by operator Dr. Maeda and a procedure LADG (laparoscopic assisted distal gastrectomy) by operator Dr. Sekiguchi.

The example in FIG. 2 describes contents of the end process on the recording apparatus 2e and the video processor 2a when the procedure end is instructed by the operation on the end display on the procedure laparoscopic cholecystectomy by operator Dr. Maeda. That is, for the procedure laparoscopic cholecystectomy by Dr. Maeda, recording of the recording apparatus 2e is stopped, the folder of the recording apparatus 2e is closed and an end of the procedure for the video processor 2a is notified as the end process.

The recording apparatus 2e is configured to create a folder for each patient and record various types of information such as an endoscope image of a patient in the created folder for each patient. "Close folder" is an end process for closing a folder recorded at an end of a medical action on the patient and preventing recording of information of other patients.

An endoscope 16 is connected to the video processor 2a. The endoscope 16 is inserted into a subject to pick up an image of the subject and output an image pickup signal to the video processor 2a. The video processor 2a is enabled to generate an endoscope image through signal processing to the image pickup signal. The video processor 2a manages the patient information. The patient information is accumulated in a server in a hospital which is not shown (in-hospital server) and the video processor 2a is configured to read from the in-hospital server patient information on a patient to whom the next medical action is applied and manage the patient information when a medical action for a certain patient is ended. Note that the control section 11 is configured to be able to read the patient information from the video processor 2a and give the patient information to the recording apparatus 2e, thus allowing the recording apparatus 2e to record the patient information in a folder for each patient.

The procedure end notification to the video processor 2a plays the role of a trigger for the video processor 2a to switch patient information. The control section 11 notifies the video processor 2a of an end of the procedure, and the video processor 2a thereby reads patient information of the patient to whom the next medical action is applied from the in-hospital server. Note that when no patient to whom the next medical action is applied exists, the video processor 2a simply resets the patient information. By notifying the video processor 2a of an end of the procedure, the video processor 2a switches the patient information and prevents mismatch between another patient information and the patient to whom medical action is actually applied.

Regarding the procedure LADG by Dr. Sekiguchi, recording of the recording apparatus 2e is stopped, the folder of the recording apparatus 2e is closed, an end of the procedure is notified to the video processor 2a, the TV conference system is disconnected and power of the loop camera is turned off as the end process.

Note that the end process other than the end process described in FIG. 2 includes initialization of a video switcher. In the operating room, not only photographing by the endoscope 16 but also photographing by various types of cameras is performed, and the video switcher allows the user to select a monitor on which each image is displayed from among monitors in the operating room. Such a setting is initialized when the video switcher is initialized. Note that the patient information may be set not only in the recording apparatus 2e and the video processor 2a but also in other operated devices 2 and the patient information of the operated devices 2 can also be cleared in the end process.

Thus, the control section 11 displays, for each operator or each procedure, an end time setting item list display which is an operation display for executing various types of end processes and thereby helps the operator or the like reliably execute an end process desired by the operator or the like.

Figure 4:
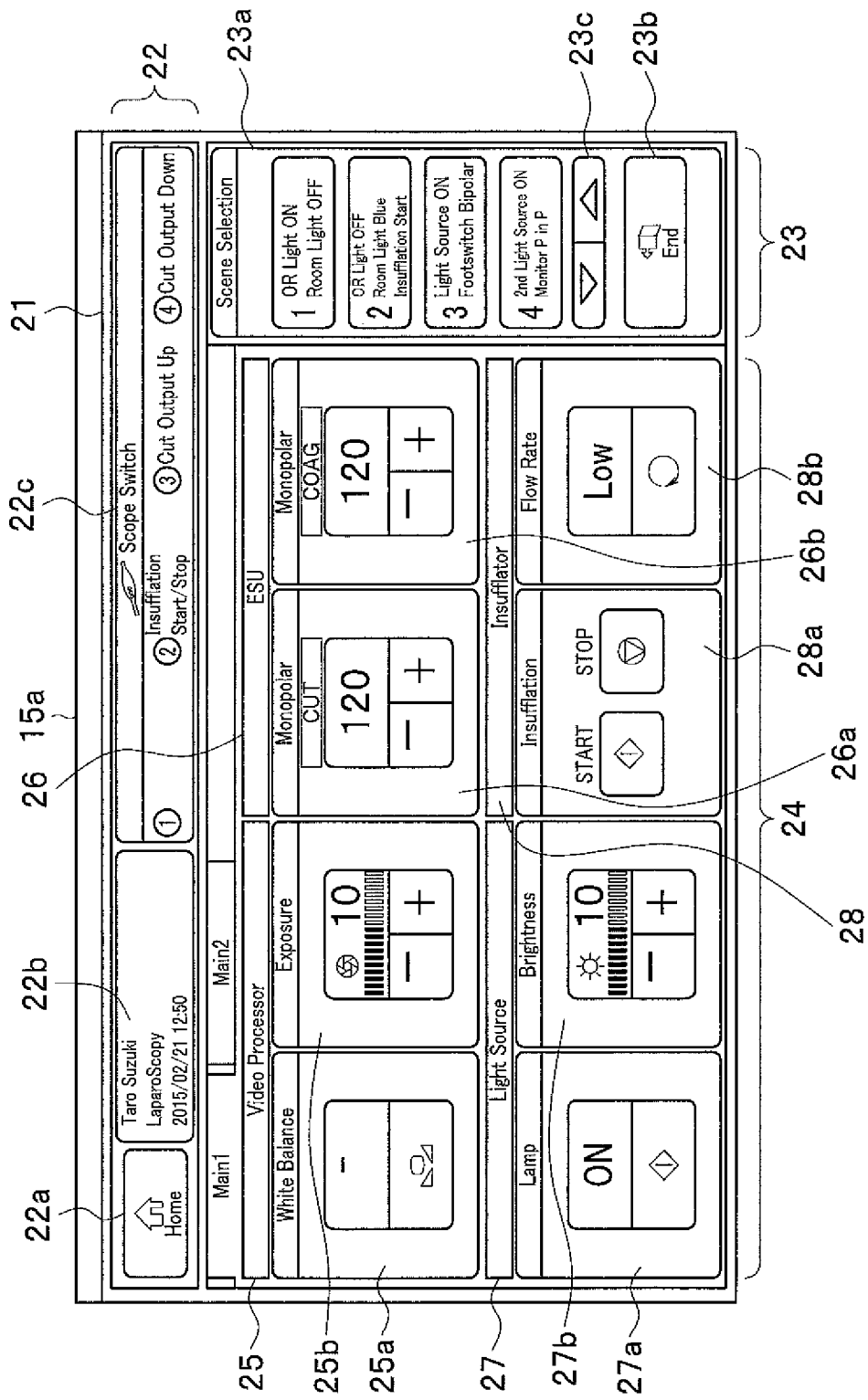
FIG. 4 is an explanatory diagram illustrating an operation display for operating an operated device 2.
Figure 5:
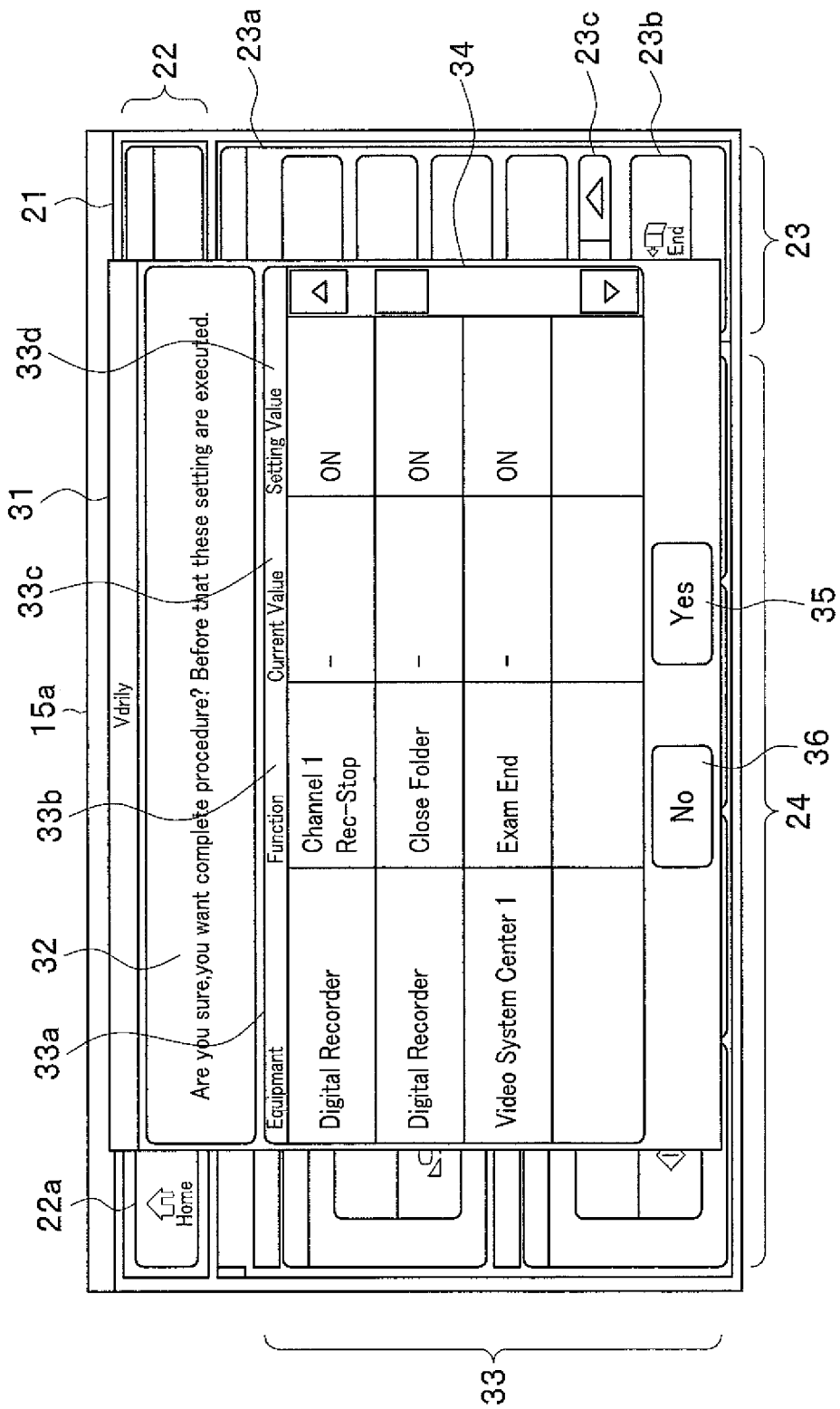
FIG. 5 is an explanatory diagram illustrating an end time setting item list display.

Next, operation of the embodiment in such a configuration will be described with reference to FIG. 3 to FIG. 5. FIG. 3 is a flowchart for describing operation of the embodiment. FIG. 4 and FIG. 5 are explanatory diagrams illustrating an example of an operation display; FIG. 4 illustrating an operation display for operating the operated device 2 and FIG. 5 illustrating an end time setting item list display.

When the power of the system controller 10 is turned on, the control section 11 reads display data of the operation display from the recording section 13 and gives the display data to the display I/F 14. The display I/F 14 generates an operation display based on the display data and causes the display screen of the operation panel 15 to display a predetermined initial screen. For example, the initial screen displays an operator selection screen and a procedure selection screen for the user to log on the system controller 10. The nurse or the like selects an operator and a procedure, and logs on the system controller 10 for a centralized operation of the operated device 2 by the system controller 10. The control section 11 sets an operator based on the operation in step S1 and sets a procedure based on the operation in step S2.

In step S3, the control section 11 reads information corresponding to the set operator and procedure from the recording section 13. The control section 11 exchanges data with the operated device 2 via the communication I/F 12 and also acquires information relating to the condition of the operated device 2. The control section 11 generates data of operation display to be displayed on the display screen 15a of the operation panel 15 based on the information acquired from the recording section 13 and the operated device 2 and gives the data to the display I/F 14. The display I/F 14 generates an operation display under the control of the control section 11 and gives the operation display to the operation panel 15. Therefore, the operation display is displayed on the display screen 15a of the operation panel 15 (step S4).

FIG. 4 illustrates an example of the operation display in the case. The operation display in FIG. 4 includes an upper display region 22 and a right display region 23 which are always displayed while the system controller 10 is logged on and also includes a central display region 24, a display of which changes depending on a selected menu.

A home button 22a for indicating transition to a home screen, a display 22b displaying an operator, a procedure and a date and time, and a scope switch display 22c for setting a function to be assigned to a scope switch which is not shown provided for the endoscope 16 are displayed in the upper display region 22. In the example in FIG. 4, the scope switch display 22c shows functions assigned to four switches of the endoscope 16.

A procedure selection button group 23a for selecting each scene of a procedure and an end button 23b ("End") for executing an end process are displayed in the right display region 23. In the example in FIG. 4, four selection buttons 1 to 4 are displayed in the procedure selection button group 23a and by operating a vertical switching button 23c, a selection button for selecting other registered scenes can be displayed.

In the central display region 24, items to be displayed are changed according to a selected menu. In the example in FIG. 4, the central display region 24 includes a display region 25 for a set value and changing the set value of a video processor 2a ("Video Processor"), a display region 26 for a set value and changing the set value of an electric knife apparatus ("ESU") 2d, a display region 27 for a set value and changing the set value of a light source apparatus 2b ("Light Source") and a display region 28 for a set value and changing the set value of an insufflator 2c ("Insufflator").

The display region 25 is provided with a display region 25a for a set value and changing the set value of white balance ("White Balance") of the video processor 2a and a display region 25b for a set value and changing the set value of an aperture ("Exposure"). Furthermore, the display region 26 is provided with a display region 26a for a set value and changing the set value of the output of the electric knife apparatus 2d at the time of dissection ("CUT") and a display region 26b for a set value and changing the set value at the time of coagulation ("COAG").

The display region 27 is provided with a display region 27a for an ON/OFF set value and changing the set value of the light source apparatus 2b and a display region 27b for a set value and changing the set value of brightness ("Brightness"). Furthermore, the display region 28 is provided with a display region 28a for a set value and changing the set value of starting and ending operation of the insufflator 2c and a display region 28b for a set value and changing the set value of a flow rate ("Flow Rate").

An upper portion and a lower portion of a rectangular frame of each display region 25a, 25b, 26a, 26b, 27a, 27b or 28b indicate a current set value and an operation portion for changing the set value respectively. For example, the display region 26a shows that output at the time of dissection is currently set to 120 W and that the output can be decreased by touching a minus mark portion of the lower operation portion and the output can be increased by touching a plus mark portion of the lower operation portion. On the other hand, in the display region 28a, the left rectangular frame is an operation button for starting operation of the insufflator and the right rectangular frame is an operation button for ending operation of the insufflator.

When the operator or the like touches the touch panel on each portion of the operation display, an operation signal corresponding to each touched portion is supplied to the control section 11. The control section 11 thereby performs control corresponding to the touch operation.

Here, assume that the medical action on the predetermined patient ends. The operator or the like performs an end operation of touching the end button 23b on the operation display to end the procedure. In the present embodiment, the touch operation on the end button 23b as the end operation section corresponds to setting starting of a display of the end time setting item list display for executing an end process. An operation signal based on the operation is supplied to the control section 11. In step S5, the control section 11 determines whether or not the end button 23b of the procedure is touched and proceeds to step S6 when the touch operation is detected and reads information for displaying the end time setting item list display from the recording section 13. The control section 11 outputs display data of the end time setting item list display to the display I/F 14. The display I/F 14 generates and displays the end time setting item list display on the display screen 15a of the operation panel 15.

The end time setting item list display in FIG. 5 corresponds to the procedure laparoscopy (laparoscopic surgery) by the operator Taro Suzuki shown on the display 22b in FIG. 4. As shown in FIG. 5, an end time setting item list display 31 is displayed superimposed on the operation display 21 and can be displayed at the center of the display screen 15a in a large-enough size and the operator can easily check contents of the end time setting item list display 31. The end time setting item list display 31 includes a display region 32 configured to display a message indicating that a procedure is ended and a setting is executed before ending the procedure and a display region 33 configured to indicate the setting contents. The display region 33 is provided with an item 33a indicating an operated device for which an end process is set, an item 33b indicating a function, an item 33c indicating an initial value and an item 33d indicating a set value at the end time.

The example in FIG. 5 shows that an end process of stopping recording for a digital recorder which is the recording apparatus 2e on a channel 1, an end process of closing the patient folder for the digital recorder which is the recording apparatus 2e and an end process of notifying a video system center 1 which is the video processor 2a of an end of an inspection (end of a procedure) are executed as the end processes.

Note that in the end time setting item list display 31 in FIG. 5, only four items can be displayed simultaneously as the end process, but by operating a scroll bar display 34, five or more items can also be displayed for the end process. The operator or the like can check necessary end processes with reference to the end time setting item list display 31. The end time setting item list display 31 is always displayed by touching the end button 23b, thus preventing the operator or the like from forgetting to check the end process.

In step S7, the control section 11 determines whether or not a collective setting execution button is pressed (operated). A "Yes" button display 35 and a "No" button display 36 are displayed in the end time setting item list display 31, and when the "Yes" button display 35 is touched, the control section 11 determines that the collective setting execution button is operated. On the other hand, when the "No" button display 36 is touched, the control section 11 determines that the procedure end operation is canceled, erases the display of the end time setting item list display 31, displays the original operation display 21 and returns the process to step S5.

When the operator or the like touches the "Yes" button display 35, the control section 11 shifts the process to step S8 and executes a collective setting. That is, the control section 11 executes each end process set in the end time setting item list display 31.

Thus, when an end operation is performed at the end of a procedure in the present embodiment, the end time setting item list display showing a list of necessary items as end process at an end of the procedure is displayed. Therefore, the operator or the like can reliably check and execute the necessary end process. When an actual surgery work flow is taken into consideration, an end button for ending the procedure is necessarily operated at the end of the procedure. In the present embodiment, the operation makes it possible to display a necessary setting item list at the end of surgery, make the setting and execute the setting in a single operation and thereby execute the necessary setting at the end of procedure simply and without forgetting to do so.

Second Embodiment

Figure 6:
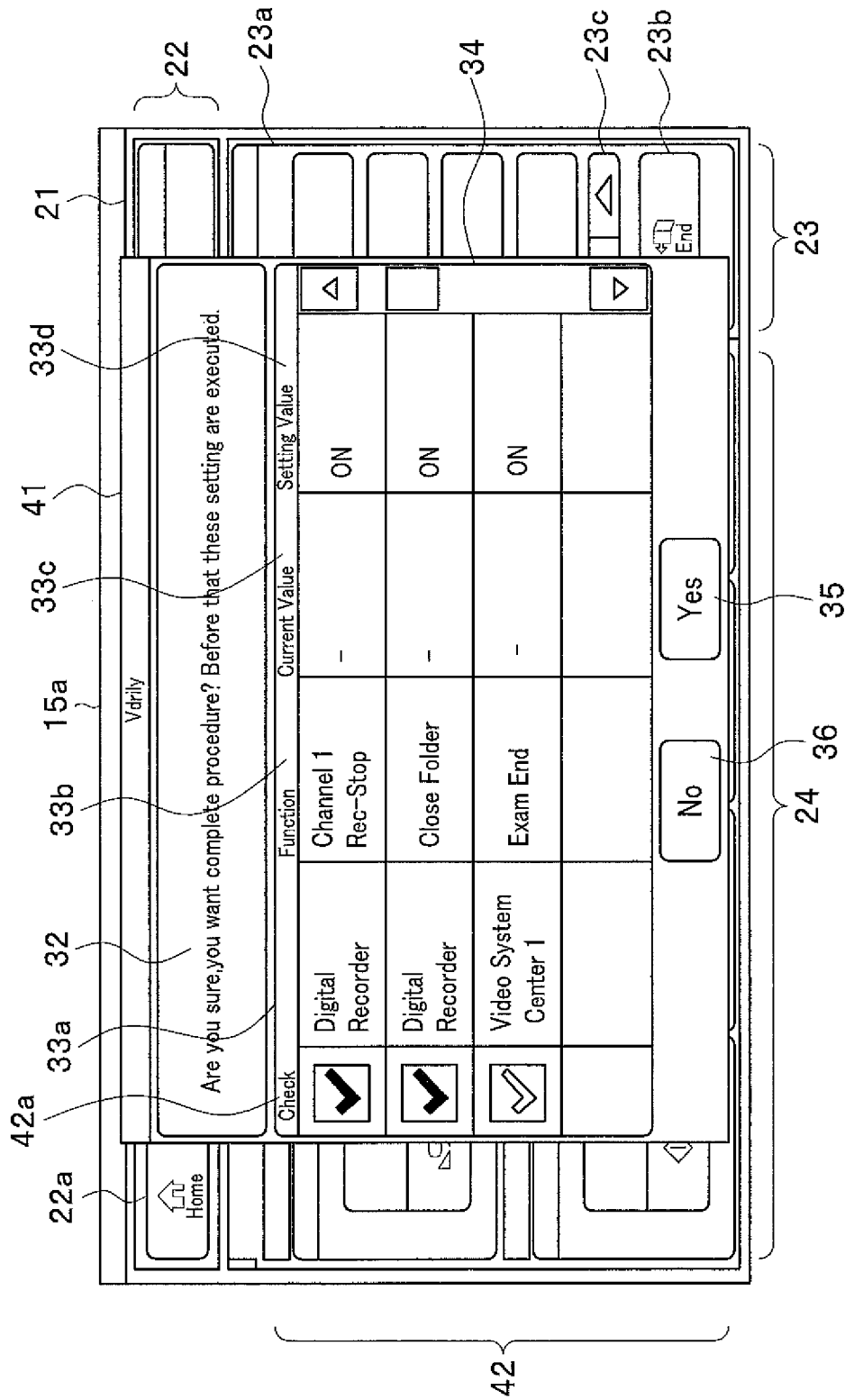
FIG. 6 is an explanatory diagram illustrating a display example of an end time setting item list display adopted in a second embodiment of the present invention.

FIG. 6 is an explanatory diagram illustrating a display example of an end time setting item list display adopted in a second embodiment of the present invention. A hardware configuration in the present embodiment is similar to the hardware configuration in the first embodiment. An example has been described in the first embodiment where all setting items displayed in the end time setting item list display are executed. In contrast, the present embodiment is an example where only setting items selected by the operator or the like from among the respective setting items displayed in the end time setting item list display are executed.

In the present embodiment, the control section 11 displays an end time setting item list display 41 shown in FIG. 6. The end time setting item list display 41 is different from the end time setting item list display 31 in FIG. 5 in that a check field 42a is provided in a display region 42 indicating setting contents. The check field 42a is provided for each setting item and only setting items which are checked in the check field 42a are actually executed as the end process among the respective end processes in the end time setting item list display 41. In FIG. 6, checking is expressed by flipping of a check mark in the check field 42a and FIG. 6 shows a state in which the end processes of recording stop of the digital recorder and closing of the patient folder are ready to be executed.

When the operator or the like touches the check field 42a, checking or unchecking is possible and the operator can select items for which end processes are performed through a simple operation. The checking operation of the operator or the like is transmitted to the control section 11 and the control section 11 executes only the setting items checked in the check field 42a as the end process.

Note that in FIG. 6, the display color and display concentration may also be made to differ between checked setting items and unchecked setting items in the check field 42a.

The other components and operations are similar to the components and operations of the first embodiment.

Thus, in the present embodiment, effects similar to the effects in the first embodiment can be obtained. Furthermore, the present embodiment has an advantage that the operator can select setting items of an end process.

Note that although an example has been described in the above embodiment where setting items for an end process are recorded for each operator or for each procedure and an end time setting item list display recorded for each operator or for each procedure is displayed, it is also possible to read setting items for all end processes that can be performed at the end time and display the setting items as an end time setting item list display so that the operator or the like selects setting items of a desired end process from among the setting items.

Third Embodiment

Figure 7:
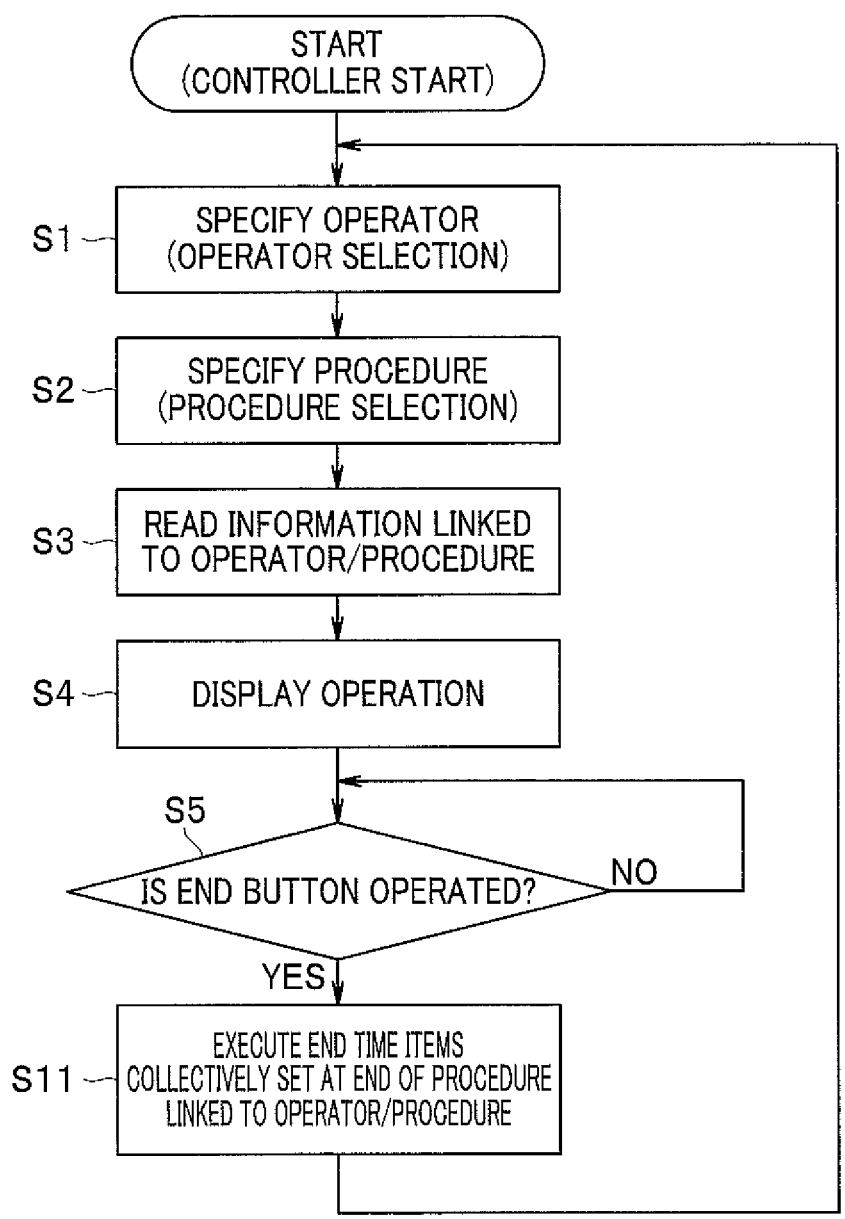
FIG. 7 is a flowchart illustrating an operation flow according to a third embodiment of the present invention.

FIG. 7 is a flowchart illustrating an operation flow according to a third embodiment of the present invention. In FIG. 7, steps identical to the steps in FIG. 3 are assigned identical reference numerals and description of the steps will be omitted. A hardware configuration of the present embodiment is similar to the hardware configuration of the first embodiment. An example has been described in the first and second embodiments where the end time setting item list display is displayed through an end operation by the operator and the setting items are then executed. In contrast, in the present embodiment, respective setting items of an end process are automatically executed through an end operation without displaying any end time setting item list display.

An operation display in the present embodiment is similar to the operation displays in the first and second embodiments. In step S5, the control section 11 determines whether or not an end operation is performed through an operation of the end button 23b. When the end button 23b is operated, the control section 11 reads information on setting items of an end process corresponding to an operator and a procedure from the recording section 13 in step S11 and executes each setting item of the end process. The control section 11 causes the process to return from step S11 to step S1 and display an initial screen for setting an operator.

Figure 8:
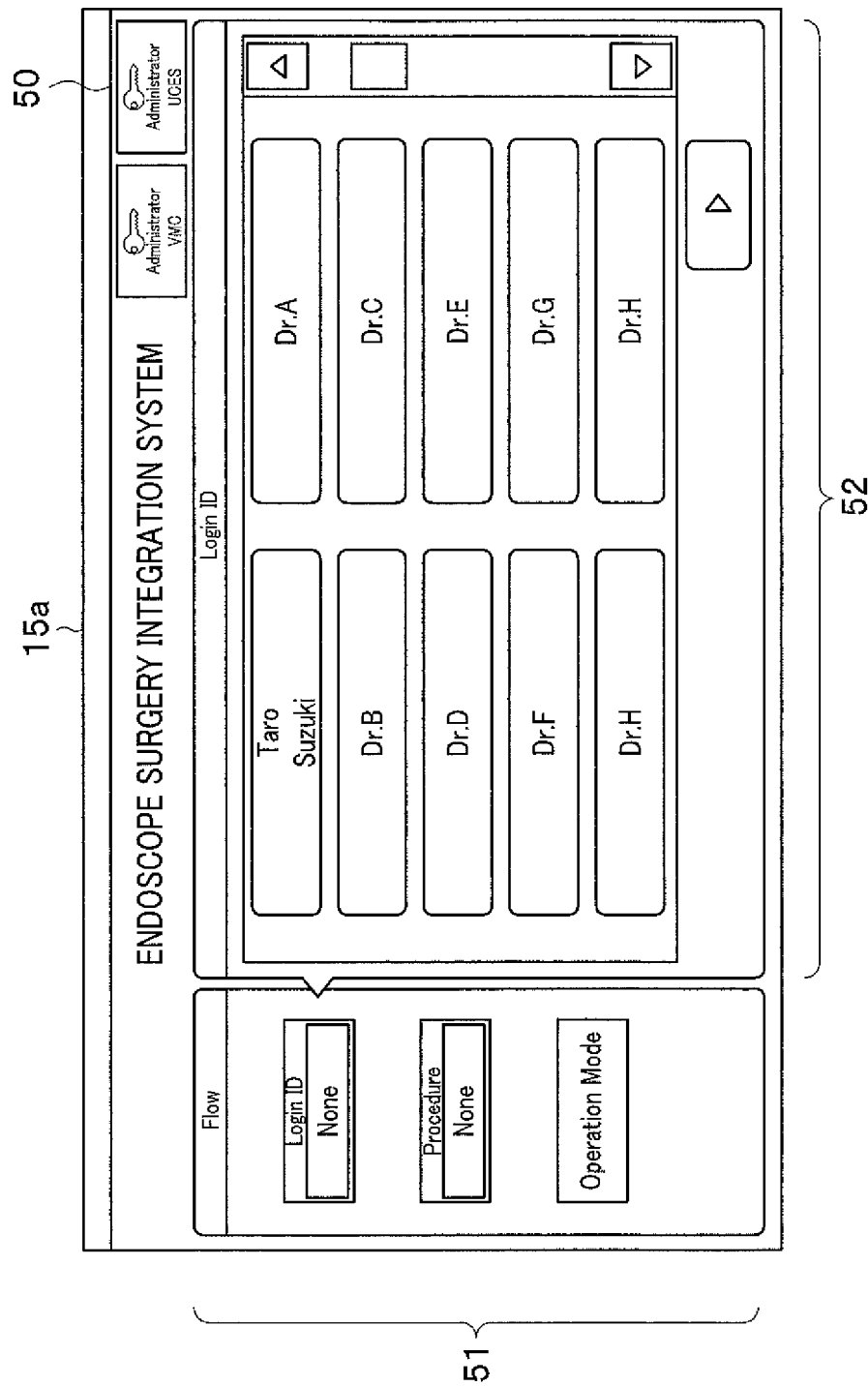
FIG. 8 is an explanatory diagram illustrating an example of an initial screen.

FIG. 8 is an explanatory diagram illustrating an example of the initial screen. The initial screen in FIG. 8 shows a screen for setting an operator, which is a screen for the setting made at the beginning at the time of logging on the system controller 10. The initial screen 50 includes a display region 51 showing processes at log-on on the left of a display screen 15a and a display region 52 for specifying an operator on the right of the display screen 15a. The nurse or the like touches a frame of the display region 52 in which operators are described, and can thereby select an operator.

The other components and operations are similar to the components and operations of the first embodiment.

Thus, effects similar to the effects in the first embodiment can also be obtained in the present embodiment. Furthermore, in the present embodiment, an end process is automatically executed without the operator performing any operation after the end operation, and it is thereby possible to reliably prevent the operator from forgetting to execute the end process.

(Modification)

Figure 9:
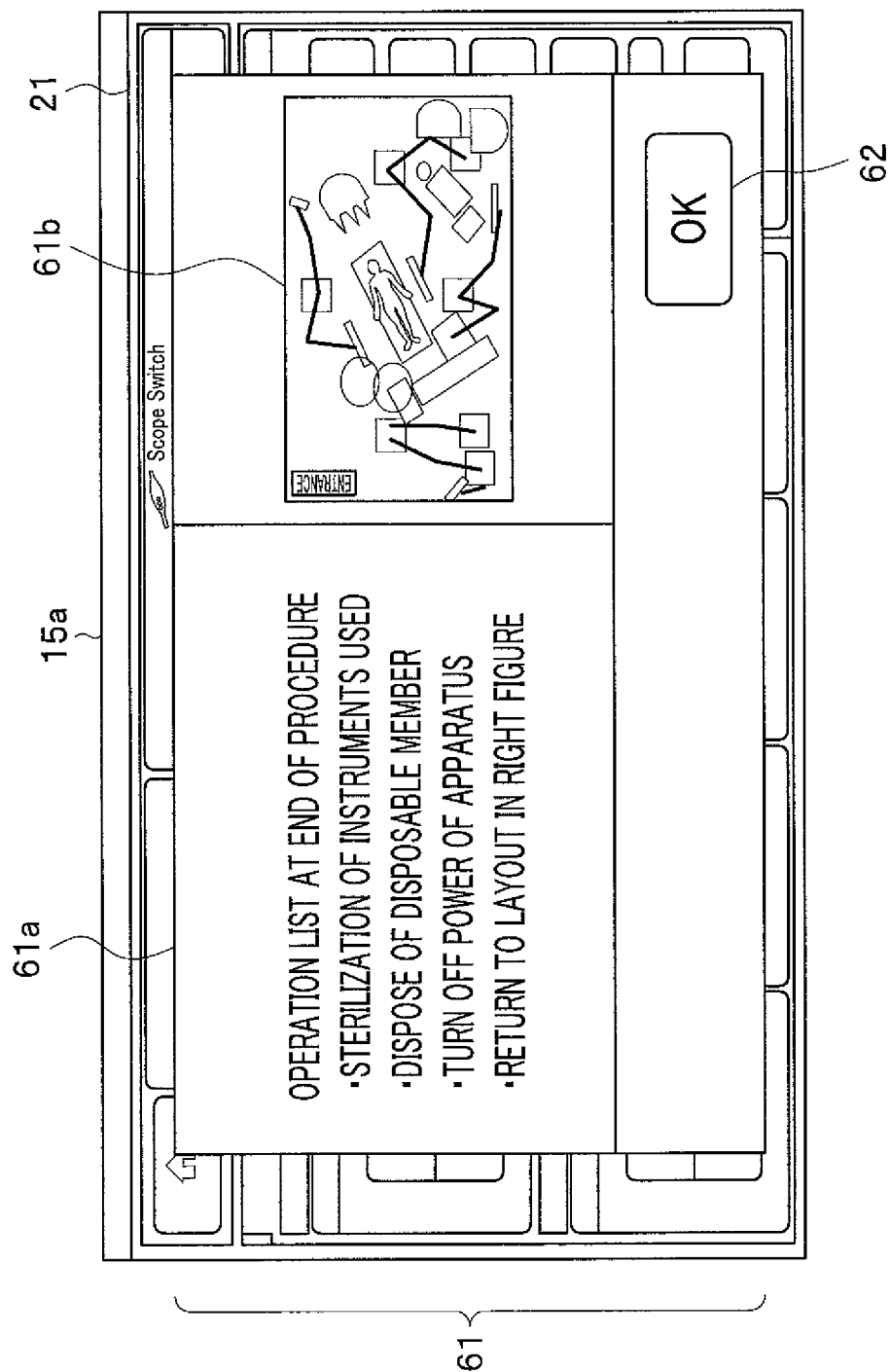
FIG. 9 is an explanatory diagram illustrating a modification.

FIG. 9 is an explanatory diagram illustrating a modification. In the present modification, when not only an end process on each unit of the operated device 2 but also an end operation is performed, a list of necessary operations is displayed on the display screen 15a at an end of a procedure. FIG. 9 shows a display example on the display screen 15a in the case and an operation list display 61 is displayed on the operation display 21. The operation list display 61 includes a display region 61a showing an operation list using characters on the left and a display region 61b showing a layout of an operating room using a schematic image.

Using the operation list display 61, the nurse or the like can check operations at an end of a procedure and reliably prevent the nurse from forgetting to perform operations. The nurse or the like touches an OK button 62, and can thereby erase the display of the operation list display 61.

In such a way, in the present modification, it is possible not only to set operated devices but also to support the operator and nurse or the like so as to reliably execute operations to be performed at the end of procedure.

Figure 10:
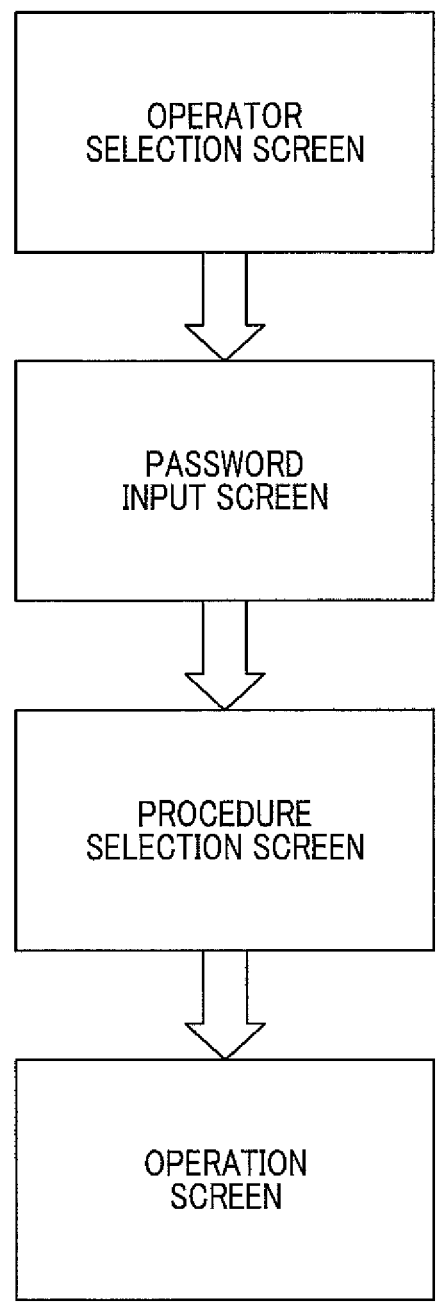
FIG. 10 is an explanatory diagram illustrating screen transition in a conventional example.

According to the above description, the system controller 10 was described that the system controller 10 is enabled to perform a centralized operation on an operated device by performing log-on to select an operator and a procedure. Therefore, when power of the system controller 10 is turned on, an operator selection screen for selecting an operator is not displayed on the operation panel 15 first. That is, as shown in FIG. 10, after power is turned on, the operation panel 15 conventionally displays an operator selection screen first, then displays a password input screen, displays a procedure selection screen and then displays an operation screen for performing various types of operation.

However, during actual surgery, it is a common practice that a layout change is conducted to change a layout of devices in the operating room such as a monitor and an anesthetization system along with the procedure. For example, a layout image is read from a USB memory or the like, displayed on the operation panel 15, and a layout change is checked while viewing the image displayed. However, to display the layout image, the operation screen needs to be displayed, a log-on process to select an operator or the like is required, and it may take much time and labor to display the layout image.

Figure 11:
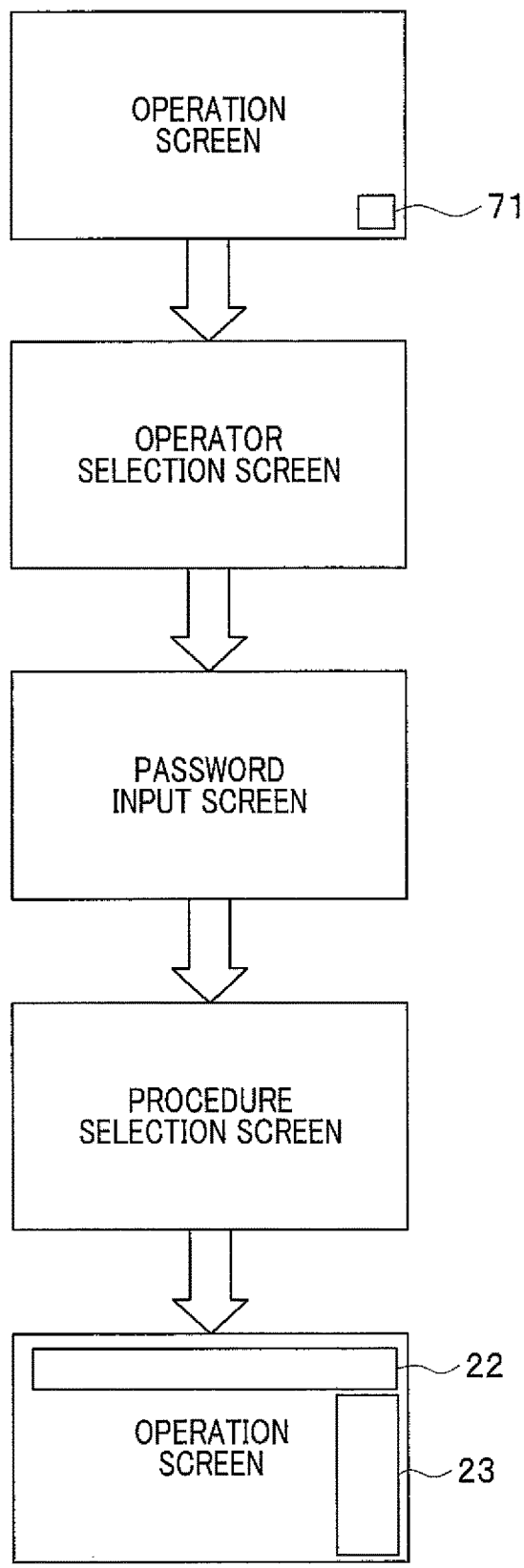
FIG. 11 is an explanatory diagram illustrating screen transition.

Therefore, immediately after the power of the system controller 10 is turned on, the operation screen may be displayed first. A call button for an operator selection screen is displayed on the operation screen. FIG. 11 is an explanatory diagram illustrating screen transition in the case.

That is, as shown in FIG. 11, after power is turned on, an operation screen is displayed on the operation panel 15 first. Using the operation screen, it is possible to perform various types of processes such as a display process on the aforementioned layout image. Next, an operator selection screen is displayed by operating an operator selection screen call button 71 on the operation screen. When an operator is selected, a password input screen is displayed, a procedure selection screen is displayed and an operation screen for performing various types of operations is then displayed.

Note that the operation screen displayed after the procedure selection screen includes the fixed upper display region 22 and the right display region 23, whereas the operation screen displayed in an initial state includes no region 22 or 23, but includes the operator selection screen call button 71.

As shown in FIG. 11, by displaying the operation screen immediately after turning on power, the nurses or the like can perform various types of operation immediately after turning on power and simply call individual data of the operator or the like registered in advance.

Note that through a setting operation, the system controller 10 may be configured such that display order in which the respective screens (operation screen, operator selection screen, password input screen and procedure selection screen) are displayed after turning on the power of the system controller 10 can be set as appropriate.

ON/OFF of suctioning of the insufflator 2c can be controlled by a foot switch which is not shown and ON/OFF of suctioning can also be controlled by an operation button displayed on the operation panel 15. For example, the insufflator 2c may be operated to suction smoke produced through, for example, ablation treatment by the electric knife apparatus 2d. In such a case, it is necessary to continuously press the foot switch or continuously press the operation button displayed on the operation panel 15 over a period of the suctioning operation, which results in poor operability.

In this case, operability improves significantly if the suctioning operation of the insufflator 2c can be controlled by a scope switch relatively easily operable by the operator while viewing an endoscope image. However, the insufflator 2c and the endoscope 16 are not directly connected together, and it is not possible to directly transmit an operation signal obtained through operation of the scope switch of the endoscope 16 to the insufflator 2c. Therefore, the system controller 10 makes a setting such that ON/OFF of the suctioning operation of the insufflator 2c is assigned to the scope switch.

Figure 12:
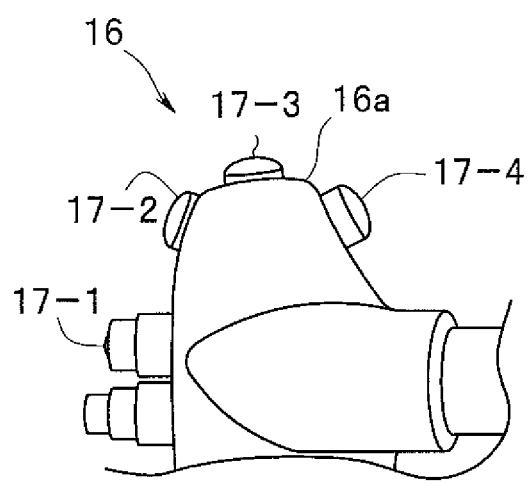
FIG. 12 is an explanatory diagram illustrating a scope switch provided for an endoscope 16.

FIG. 12 is an explanatory diagram illustrating a scope switch provided for the endoscope 16. The endoscope 16 includes an elongated insertion portion (not shown) on a distal end side and an operation portion 16a for operating the endoscope 16 on a proximal end side as shown in FIG. 12. Four scope switches 17-1 to 17-4 are disposed on the operation portion 16a. The endoscope 16 is configured to be driven by the video processor 2a and operation signals are supplied to the video processor 2a through operations of the scope switches 17-1 to 17-4. The video processor 2a is configured to control the respective sections of the endoscope 16 based on the inputted operation signals.

The control section 11 of the system controller 10 is connected to the video processor 2a via the communication I/F 12 and is configured to assign the functions of the scope switches 17-1 to 17-4 to the video processor 2a. For example, ON/OFF of the suctioning operation of the insufflator 2c is assigned to the scope switch 17-3. For example, it is possible to perform control so as to turn OFF the suctioning operation from ON and turn ON the suctioning operation from OFF every time the scope switch 17-3 is pressed once.

Figure 13:
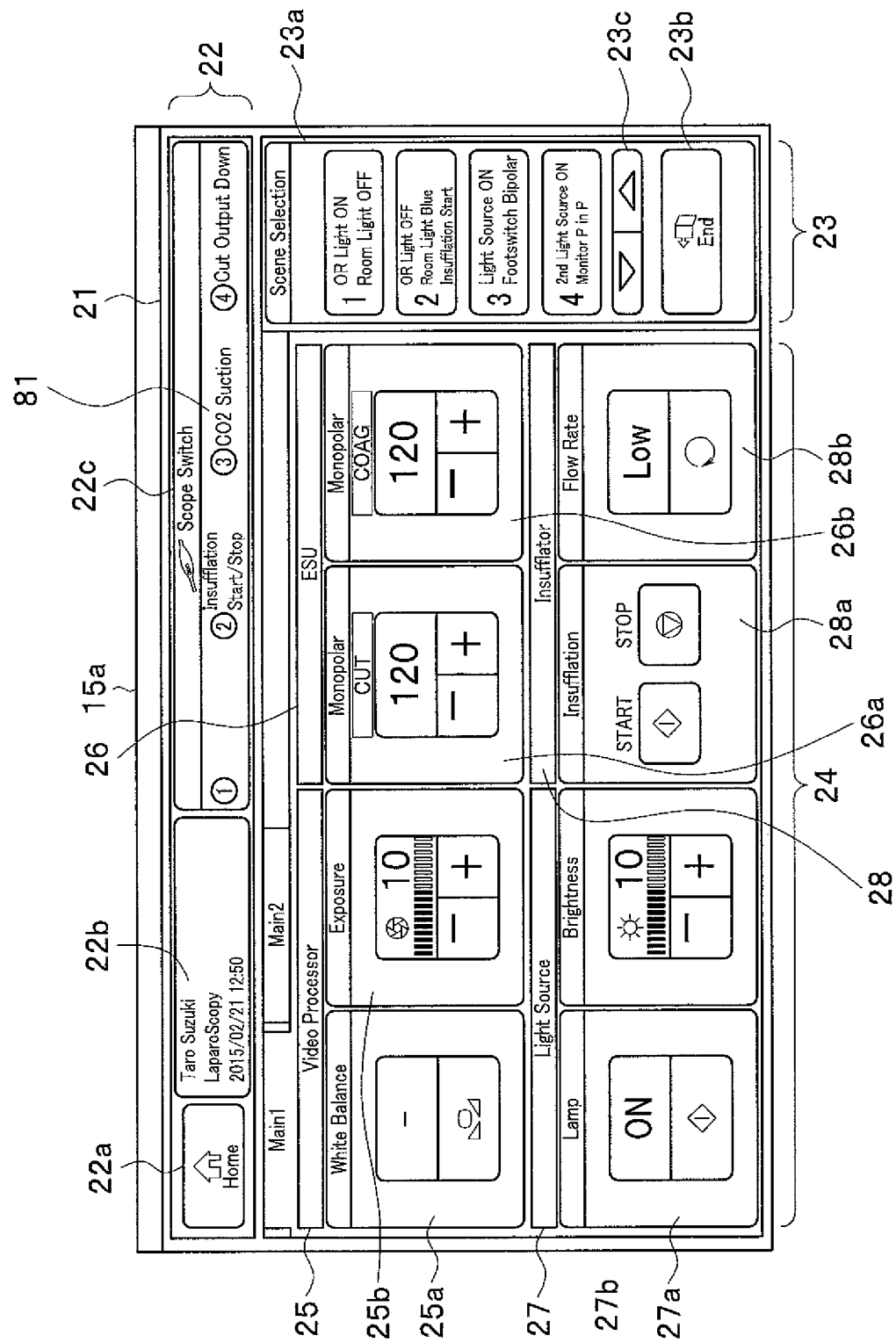
FIG. 13 is an explanatory diagram illustrating an example of operation display in the case.

FIG. 13 is an explanatory diagram illustrating an example of operation display in the case. FIG. 13 illustrates an operation display 21 similar to the operation display 21 in FIG. 4 and the scope switch display 22c shows functions to be assigned to the scope switches 17-1 to 17-4 using circled numbers 1 to 4. A display 81 that follows the circled number 3 shows that ON/OFF of the suctioning operation ($CO_2$ Suction) is assigned to the scope switch 17-3.

Using the system controller 10 as described above, it is possible to assign ON/OFF of the suctioning operation of the insufflator 2c to the scope switch 17-3 of the endoscope 16. Therefore, the operator can perform suctioning by the insufflator 2c through the pressing operation of the scope switch 17-3 while checking a situation with endoscope images using the endoscope 16. It is not necessary to continuously press the scope switch 17-3 for a suction period, which provides excellent operability. The state in which the functions of the scope switches 17-1 to 17-4 are assigned is displayed on the display screen 15a of the operation panel 15 and the operator can easily check that the suctioning function or the like is assigned to the scope switch.

The present invention is not limited to the respective embodiments described above as the embodiments are, but can be implemented by modifying components without departing from the spirit and scope of the invention in the stage of implementation. Furthermore, various inventions can be formed by combining a plurality of components disclosed in the above described embodiments as appropriate. For example, several components may be deleted from among all the components shown in the embodiments. Furthermore, components among different embodiments may be combined as appropriate.

What is claimed is:

1. A centralized control apparatus configured to operate in a centralized manner, a plurality of operated devices used in a medical action, the centralized control apparatus comprising:
    a display device displaying a graphical user interface, the display device being configured to:
        specify at least one of an operator and a procedure; and
        receive an inputted end operation from the operator to end a centralized operation of one of the plurality of operated devices operated by the operator when the medical action ends;
    a memory configured to store information in association with at least one of the operator and the procedure, the information including a list of setting items that require end processes to be performed at the end of the medical action; and
    a processor configured to, upon receiving the inputted end operation, acquire, from the memory, the information including the list of setting items that require the end processes to be performed at the end of the medical action, and display and execute setting items included in the list of setting items on the plurality of operated devices based on the specified at least one of the operator and the procedure.

2. The centralized control apparatus according to claim 1, wherein the processor is configured to:
control the display device to display the list of the acquired setting items of the end process,
receive authorization to execute the acquired setting items of the end process, and
execute the setting items.

3. The centralized control apparatus according to claim 2, wherein the processor executes only setting items selected through a user operation from among the setting items of the end process displayed in the list.

4. The centralized control apparatus according to claim 2, wherein the processor is configured to execute the setting items after displaying the acquired setting items of the end process displayed in the list, and subsequently display an initial screen.

5. The centralized control apparatus according to claim 1, wherein the processor is configured to control the display device to display an initial screen after executing the setting items of the end process.

6. The centralized control apparatus according to claim 1, wherein when the inputted end operation is received, the processor is configured to control the display device to display a presentation screen on which contents of necessary operations are presented when the medical action ends.

7. A centralized control apparatus configured to operate in a centralized manner, a plurality of operated devices used in a medical action, the centralized control apparatus comprising:
a display device displaying a graphical user interface, the display device being configured to:
specify an operator;
specify a procedure;
receive an inputted end operation from the operator to end a centralized operation of one of the plurality of operated devices operated by the operator when the medical action ends;
a memory configured to store information in association with a combination of the operator and the procedure, the information including a list of setting items that require end processes to be performed at the end of the medical action; and
a processor configured to, upon receiving the inputted end operation, acquire, from the memory, the information including the list of setting items that require the end processes to be performed at the end of the medical action, and display and simultaneously execute all of the setting items included in the list of setting items on the plurality of operated devices based on the specified at least one of the operator and the procedure.

* * * * *